United States Patent [19]

Nishikawa

[11] Patent Number: 4,943,735
[45] Date of Patent: Jul. 24, 1990

[54] APPARATUS FOR MEASURING CONCENTRATION OF LIQUID DEVELOPER

[75] Inventor: Masaji Nishikawa, Hachioji, Japan

[73] Assignee: Olympus Optical Co., Ltd., Japan

[21] Appl. No.: 204,494

[22] Filed: Jun. 9, 1988

Related U.S. Application Data

[63] Continuation-in-part of Ser. No. 828,234, Feb. 11, 1986, abandoned.

[30] Foreign Application Priority Data

Feb. 18, 1985 [JP] Japan .............................. 60-031201

[51] Int. Cl.⁵ .......................................... G01N 21/01
[52] U.S. Cl. .................................. 250/573; 356/440; 250/576
[58] Field of Search ............................. 250/573, 576; 356/436–437, 440–442; 73/861.04; 141/324; 137/574

[56] References Cited

U.S. PATENT DOCUMENTS

| | | | |
|---|---|---|---|
| 3,126,906 | 3/1964 | Touzalin et al. | 137/574 |
| 4,021,120 | 5/1977 | Muller et al. | 250/573 |
| 4,072,424 | 2/1978 | McMullan et al. | 250/573 |
| 4,135,100 | 1/1979 | Harada et al. | 250/573 |
| 4,228,678 | 10/1980 | Slaton | 250/573 |
| 4,534,647 | 8/1985 | Gross et al. | 356/440 |

*Primary Examiner*—Edward P. Westin
*Attorney, Agent, or Firm*—Ostrolenk, Faber, Gerb & Soffen

[57] ABSTRACT

Apparatus for measuring concentration of liquid developer or the like includes a holding member formed with an opening in which the liquid to be measured is retained. The holding member is driven to pass through a measuring station in which a photoelectric detector is disposed. The detector determines the amount of light transmitted through the liquid retained in the opening, thus measuring the concentration of colored component in the liquid.

5 Claims, 5 Drawing Sheets

FIG. 5
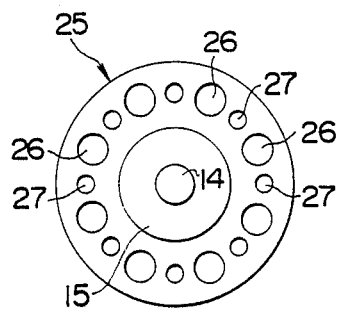
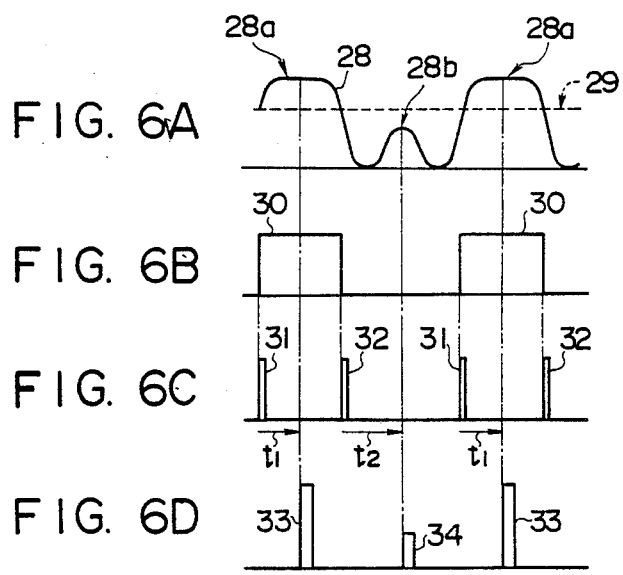
FIG. 6A
FIG. 6B
FIG. 6C
FIG. 6D
FIG. 7A
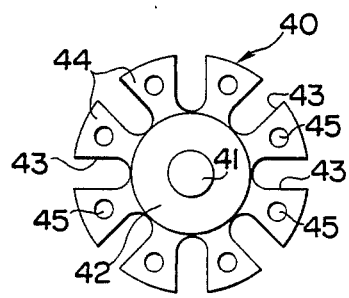
FIG. 7B
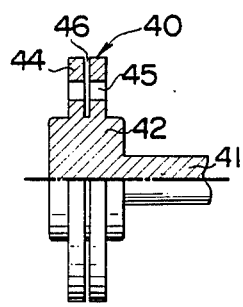

FIG. 13A
(PRIOR ART)
FIG. 13B
(PRIOR ART)
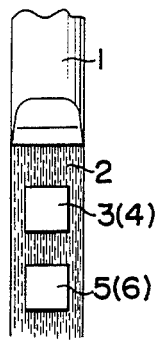
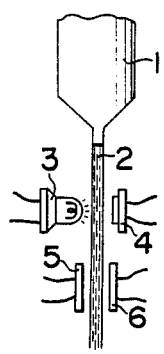

APPARATUS FOR MEASURING CONCENTRATION OF LIQUID DEVELOPER

This is a continuation-in-part of Ser. No. 828,234, filed Feb. 7, 1986, now abandoned.

BACKGROUND OF THE INVENTION

The invention relates to an apparatus for measuring the concentration of a liquid, and more particularly, to such apparatus which measures the concentration of colored fine grains contained in a liquid developer.

As is well recognized, a liquid developer comprises a dispersion of colored fine grains in a liquid dispersion medium, and is usually used to develop an electrostatic latent image. As the developing process proceeds, the colored fine grain component in the liquid developer is consumed. Alternatively, when the liquid developer is allowed to stand over a prolonged period of time, the dispersion medium becomes vaporized, and the proportion of colored fine grains mixed with the dispersion medium or the concentration thereof may change. Thus, there arises a problem that the developing process is not stabilized. In order to maintain the liquid developer at a constant concentration, the concentration may be determined photoelectrically, and either a concentrating toner or dispersion medium (carrier solution) may be supplied in response to the result of the measurement. In these instances, colored fine grains or toner particles may be deposited on the surface of a concentration measuring cell or a photoelectric sensor, causing an error in the measurement.

The problem may be eliminated by an apparatus for measuring the concentration of a developer, as disclosed in Japanese Laid-Open Patent Application No. 63,243/1981, for example. Such arrangement is illustrated in FIGS. 13A and 13B. As shown, a liquid developer is introduced into a flat nozzle 1 which is disposed in a circulating path therefor. As the developer is projected from the flat end of the nozzle 1, it forms a thin liquid film 2. Accordingly, a light source 3 and a photoelectric cell 4 together with an aligned pair of electrodes 5 and 6 are disposed on opposite sides of the liquid film 2. In this manner, the concentration of the developer is photoelectrically detected by the combination of the source 3 and the cell 4, but because the thickness of the liquid film 2 tends to be unstable, the pair of electrodes 5 and 6 is used to measure the capacitance across the electrodes to calculate the thickness of the liquid film 2 therefrom, thus providing a correction to the result obtained from the cell 4.

An advantage of the described apparatus is the fact that no inconvenience is caused by the deposition of toner particles on a measuring unit to cause an error in the measurement of the concentration. However, since the photoelectric unit is spaced from the film thickness determining unit, there is no assurance that the liquid film 2 will be maintained in the same configuration thereacross, again causing an error. In the cited application, there is disclosed a capacitance technique and an orthogonal projection technique to determine the film thickness. However, both techniques are incapable of determining the film thickness with a high degree of precision. In summary, it is difficult to determine the concentration to a high degree of precision with the conventional arrangements.

SUMMARY OF THE INVENTION

In view of the foregoing, it is an object of the present invention to provide an apparatus for precisely measuring the concentration of the liquid developer while retaining a maintenance advantage and which is capable of arbitrarily presetting a film thickness of a liquid to be determined in accordance with the characteristics of the liquid. According to the invention, the concentration of a liquid under test is determined by separately measuring the amount of light transmission through a liquid film formed in each one of openings in an independent manner.

The invention enables the measurement of concentration to a high degree of precision, assures a stable operation over a prolonged period of use, and permits any desired liquid thickness to be established in accordance with the characteristics of the liquid, all with a simple arrangement.

BRIEF DESCRIPTION OF THE DRAWINGS

FIG. 5 is a front view of another form of developer holding member;

FIGS. 6A to 6D graphically show the waveforms of various signals when the developer holding member shown in FIG. 5 is used;

FIGS. 7A and 7B are a front view, and a side elevation, with the upper-half being shown in cross section, of a further form of developer holding member;

FIGS. 13A and 13B are a front view and a side elevation of a conventional apparatus for measuring concentration.

DETAILED DESCRIPTION OF PREFERRED EMBODIMENTS

Figure 1:
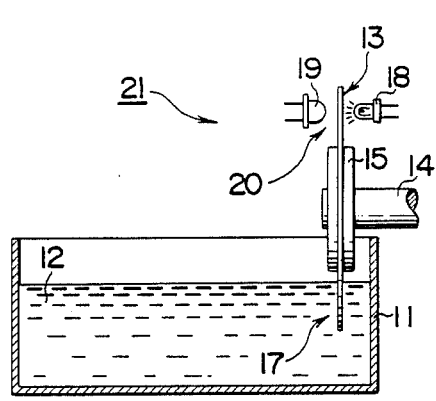
FIG. 1 is a schematic side elevation, partly in section, of an apparatus for measuring concentration according to one embodiment of the invention.
Figure 2:
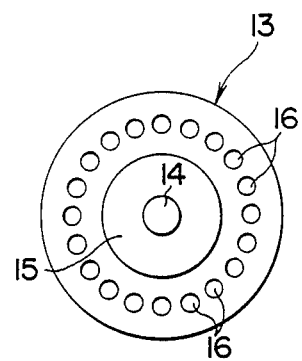
FIG. 2 is a front view of a developer holding member shown in FIG. 1.

Referring to FIG. 1, there is shown an apparatus 21 for measuring concentration according to one embodiment of the present invention in a schematic cross section. The apparatus 21 includes a developer vessel 11 which is filled with a liquid developer 12. A disc-shaped developer holding member 13 is rotatably disposed above the vessel 11 being fixed to a flange 15 which is integral with a rotating shaft 14 which is in turn connected to a rotary drive, not shown. As shown in FIG. 2, the developer holding member 13 is formed with a plurality of substantially circular openings 16 which are disposed on a common circumference centered about the center of rotation of the member 13. The developer holding member 13 is disposed so that its bottom region is immersed in the liquid developer 12 contained within the vessel 11, and hence the bottom region acts as a supply 17 of the developer 12. During the rotation of the holding member 13, successive openings 16 therein pass through the liquid developer 12 to retain a quantity of the liquid developer 12 therein. In the region of the top of the holding member 13, a photoelectric detector 20 is disposed at the elevation of the openings 16, and comprises a light source 18 and a photoelectric sensor 19 which are disposed on the opposite sides of the holding member 13. Accordingly, as the openings 16 carrying the liquid developer 12 are successively moved pass the photoelectric detector 20 as the holding member 13 rotates, the detector 20 determines the concentration of the liquid developer 12.

Figure 3:
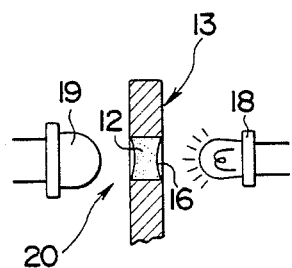
FIG. 3 is an enlarged cross section of a photoelectric detector shown in FIG. 1.
Figure 4A:
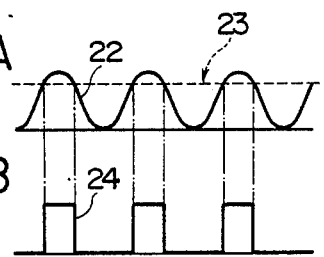
FIGS. 4A and 4B graphically show the waveforms of an output signal from a photoelectric sensor and a resulting shaped toner replenishing signal.

Referring to FIG. 3, it will be seen that the liquid developer 12 is retained within the opening 16 in the developer holding member 13 in a manner defining a meniscus cross-sectional configuration. The thickness of the film of liquid developer 12 which is retained within the opening 16 is determined by the thickness of the holding member 13, the diameter of the opening 16 and the magnitude of a surface tension acting between the holding member 13 and the liquid developer 12, and can be maintained at a greatly stabilized value. Accordingly, as light from the source 18 is transmitted through the liquid developer 12 retained in one of the openings 16, the light transmission to the sensor 19 depends on the amount of colored fine grain component or toner concentration within the liquid developer 12. The greater the toner concentration, the amount of light incident on the sensor 19 reduces while the lower the toner concentration, the amount of incident light increases. As a result, during the rotation of the holding member 13, the sensor 19 which separately detects an amount of transmitted light at each one of openings in independent manner, develops a detection signal 22 having a waveform as shown in FIG. 4a. The peak value of the signal 22 varies in a manner corresponding to the toner concentration in the developer 12. By detecting the peak value of the detection signal 22, the concentration of colored component or toner concentration in the liquid developer 12 can be accurately determined.

Figure 4B:
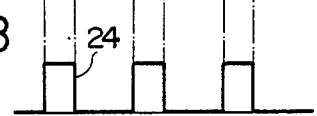

The detection signal 22 from the sensor 29 may be utilized as a signal which triggers the replenishment of a toner. In this instance, the detection signal 22 is compared against a preset reference 23, and a replenishing signal 24 is developed whenever the signal 22 exceeds the reference 23, as shown in FIG. 4B. In this manner, the signal 24 is developed when the toner concentration is less than the reference, causing the toner to be supplied to the vessel 11. When the toner is replenished and the toner concentration reaches the reference level, the signal 24 is no longer generated and the toner is no longer added. Alternatively, the signal 24 may be translated into a suitable signal to be applied to a toner replenishing unit, by employing known means which is adequate to a particular configuration of the toner replenishing unit.

Since the purpose of the openings 16 in the holding member 13 is to retain the liquid developer 12 therein in a stable manner, the liquid developer 12 cannot be retained if its diameter is too large.

Where the light source 18 and the photoelectric sensor 19, used to constitute the photoelectric detector 20, include an element of instability in their response, the developer holding member may be modified to eliminate the influences of such element. Specifically, FIG. 5 shows a modified holding member 25. The holding member 25 is formed with a first plurality of openings 27 which are disposed on a common circumference about the center of rotation of the holding member 25 and which act to retain the liquid developer 12 therein, and also with a second plurality of openings 26 of a greater size which do not allow the developer 12 to be retained therein, disposed an alternating fashion with the first mentioned openings 27. With the apparatus which employs the developer holding member 25, an opening 26 in which no developer 12 is retained and represents a free passage for the light and an opening 27 retaining the developer 12 therein successively move past the photoelectric detector 20 (see FIG. 1). Thereupon, the sensor 19 develops a detection signal 28 having a waveform as shown in FIG. 6A. As shown, the signal 28 includes a combination of a high level signal 28a resulting from the first set of opening 26 and a low level signal 28b resulting from the second set of opening 27 and having a level dependent on the toner concentration. By separating the detection signal 28 into distinct signals 28a and 28b, and by comparing the peak values of both signals, a concentration representing signal can be formed through a variety of signal processing techniques. By way of example, the detection signal 28 may be compared with a reference 29 to develop a square wave signal 30 shown in FIG. 6B which is obtained by slicing the signal 28 at the level of the reference 29. By differentiating the the square wave signal 30, pulse signals 31 and 32 shown in FIG. 6C may be developed at the rising and falling edge of the signal 30. The pulse signals 31 and 32 are delayed by time intervals t1 and t2, respectively, to provide sampling signals for the signals 28a and 28b. As a result of such sampling, there can be obtained a reference signal 33 and a sample signal 34 shown in FIG. 6D. By using a division between both signals 33 and 34, there is obtained information relating only to the concentration of the liquid developer 12 and from which factors of variation relating to the source 18 and the sensor 19 are eliminated.

Where the liquid developer 12 has a relatively high optical density, the developer holding member 13 may be formed as a simple thin plate to permit the detection of the concentration with a high degree of precision. By contrast, where the developer 12 has a relatively low optical density, the thickness of the holding member 13 may be increased to increase the thickness of a film of liquid developer 12 which is retained within the opening 16. In the latter instance, the liquid developer 12 may encounter an increased resistance when entering the opening 16 or the developer 12, once it has found its way into the opening 16, may remain therein to degrade the precision of detection. Such shortcomings are eliminated by a developer holding member shown in FIGS. 7A and 7B.

Specifically, the developer holding member 40 shown in FIGS. 7a and 7b comprises a disc which is formed integrally with the periphery of a flange 42 that is integrally formed on the free end of a rotating shaft 41 connected to a rotary drive, not shown. A plurality of notches 43 are formed in the periphery of the disc at equal intervals, thus defining a plurality of holding blades 44 around the periphery of the flange 42. Each blade 44 is formed with an opening 45 in which the liquid developer 12 is to be retained. Each blade 44 is also formed with a slit which divides the blade 44 into two portions in the thickness direction thereof. It will be seen that the provision of the slit 46 allows the opening 45 to be open in its central region through the slit. Accordingly, the supply or discharge of the liquid developer 12 into or from the opening 45 can be enhanced without degrading the retention of the liquid developer 12 therein. When forming the slit 46, it is possible to choose a narrow width for the slit 46 so that the liquid developer 12 may also be retained therein or the slit 46 may be formed to have an increased width in order to allow the developer 12 to be retained only within the opening 45. While both choices are effective, the latter arrangement assures a more reliable exchange of the liquid developer 12. However, it is to be noted that the former arrangement advantageously allows an increased output from the photoelectric detector since the thickness of the developer holding member 42 does not increase substantially. Accordingly, a choice therebetween depends on the particular application to which the device is to be put. The notches 43 formed in the holding member 40 are useful in correcting for variations in the light source 18 or output from the photoelectric sensor 19 or in providing a forced reflux of the liquid developer 12 into the slit 46.

Each apparatus has been described as being constructed so that the developer holding member 13, 25 or 40 of the respective apparatus is disposed within the developer vessel 11 (see FIG. 1). However, such disposition of the holding member may be rendered difficult in a situation where the level of the liquid developer 12 within the vessel 11 changes largely between the operating and the quiescent conditions of a recording apparatus, not shown, which uses the liquid developer 12 for purpose of recording. In addition, if the holding member remains immersed in the liquid developer 12 during the quiescent condition of the recording apparatus, colored fine grain component may be deposited on the wall of the opening over a prolonged period of use, thus reducing the diameter thereof. While the colored component is not deposited to an amount which stands in the way of light passage used for photoelectric detection, the deposition of such colored component should preferably be avoided.

Figure 8:
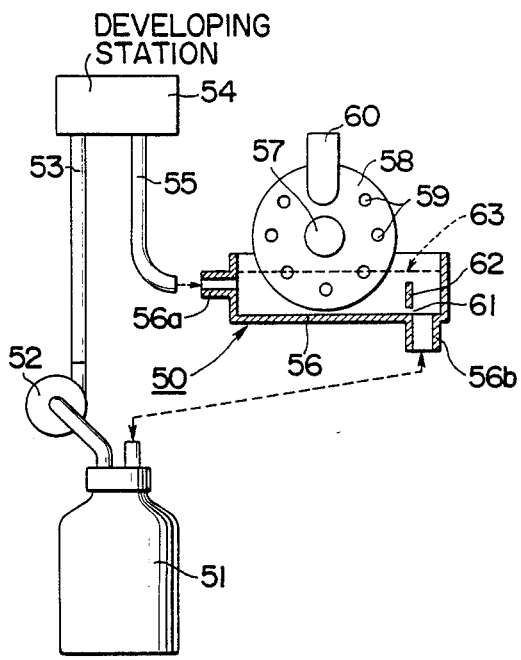
FIG. 8 is a schematic side elevation, partly in section, of an apparatus for measuring concentration according to another embodiment of the invention.

FIG. 8 shows an apparatus for measuring concentration which is designed to avoid this problem. In FIG. 8, an apparatus 50 for measuring concentration is arranged in a circulating path of the liquid developer 12 which is used in a recording apparatus, not shown. There is a high degree of freedom in arranging the apparatus 50. Specifically, when the recording apparatus is operating, the liquid developer 12 is pumped from a bottle 51 of developer by means of a pump 52 and is then fed to a developing station 54 through a feed pipe 53. The developer which has been used in the developing process at the station 54 is returned to the bottle 51 through a return pipe 55, in which the apparatus is disposed. The apparatus 50 comprises a developer vessel 56 containing a quantity of liquid developer, and a disc-shaped developer holding member 58 fixedly mounted on a rotating shaft 57 which is carried by a rotary drive, and not shown, has its bottom region immersed in the liquid developer. A photoelectric detector block 60 including a light source and a photoelectric sensor, constructed in a similar manner as mentioned previously, is disposed at an elevation which will be aligned with a top opening 59 formed in the holding member 58. The vessel 56 has an inlet fitting 56a connected to the return pipe 55 and also includes an outlet fitting 56b which may be connected to the bottle 51. A partition 62 is disposed in the vessel 56 to define a small outlet opening 61 along the bottom thereof.

During the operation of the recording apparatus, the liquid developer which has been used in the developing process is returned to the bottle 51 through the return pipe 55 and the vessel 56 of the apparatus 50. The small outlet opening 61 defined by the partition 62 disposed on the bottom of the vessel 56 is not large enough to allow a free and direct passage of the liquid developer from the pipe 55. Thus, the liquid developer introduced into the vessel 56 will partly pass through the opening 61, but the level of the developer within the vessel 56 rises rapidly to exceed a level 63, shown in broken lines, causing the developer to move beyond the top end of the partition 62, thus stabilizing the liquid level. The stabilized liquid level 63 is chosen to be sufficient to supply the liquid developer into the lower openings 59 in the holding member 58. Under this condition, the holding member 58 is driven for rotation by the rotary drive to enable the photoelectric detector block 60 to determine the concentration of the developer.

In the quiescent condition of the recording apparatus after its operation, the developer ceases to be introduced into the vessel 56 from the return pipe 55, and accordingly the developer in the vessel 56 flows out of the opening 61 to empty the vessel 56. It will thus be seen that in the quiescent condition of the recording apparatus, the holding member 58 is not immersed in the liquid developer, thus effectively preventing the deposition of the colored component contained in the developer. It is to be understood that the outlet opening 61 need not be defined by the partition 62. Alternatively, suitable means may be located in the bottom of the vessel 56 to allow the passage of the liquid developer to the outlet fitting 56b from the vessel 56. In place of using the pump 52 to pump to developer into the developer circulating system, a suction pipe connected to the return pipe 55 may be used to draw the developer into the developing station 54 under the influence of the atmospheric pressure.

Figure 9:
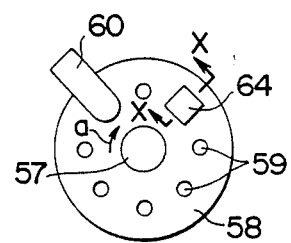
FIG. 9 is a side elevation of the apparatus shown in FIG. 8 to which a developer removal brush is attached.
Figure 10:
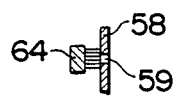
FIG. 10 is a cross section taken along the line X—X shown in FIG. 9.

In the apparatus of FIG. 8, the deposition of the colored component can be more completely prevented by removing the liquid developer from the openings 59 in the holding member 58, by using a developer removal brush 64 as shown in FIGS. 9 and 10. The holding member 58 is shown as rotating in a direction indicated by an arrow a, and in this instance, the brush 64 is disposed on the downstream side of the photoelectric detector block 60 so that the free end of the brush which is formed of a highly absorbent elastic member can be located opposite to openings 59 in the holding member 58. During operation of the photoelectric detector block 60, the brush 64 is moved away from the position where it is maintained in contact with the holding member 58, but when the operation of the photoelectric detector block has been terminated and the liquid level is lowered, the brush 64 is moved into contact with the holding member 58. Subsequent rotation of the holding member 58 allows the free end of the brush 64 to contact the openings 59 to drive the developer which has been retained therein away from the openings.

Figure 11:
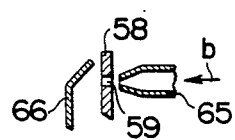
FIG. 11 is a cross section showing another form of developer removal unit.

FIG. 11 shows alternative means for removing the developer from the openings 59. Specifically, an air nozzle 65 is located opposite to one of the openings 59 so that when the air under pressure is fed into the nozzle 65 in a direction indicated by an arrow b, the air jet from the nozzle 65 blows any remaining developer from the opening 59. It is desirable that a developer trap plate 66 be disposed opposite to the air nozzle 65 to prevent a dispersion of the developer.

Figure 12:
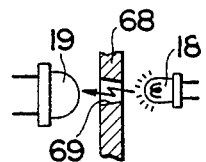
FIG. 12 is a cross section of another form of an opening formed in a developer holding member.

It should be understood that a number of changes and modifications are possible in the various apparatus of the invention mentioned above. By way of example, the internal wall of the openings 16, 26, 27, 45 may be colored to a black color or any other color which matches the colored component of the developer so that any deposition of the colored component on the inner wall of the opening cannot cause a change in the output from the photoelectric detector. Alternatively, as shown in FIG. 12, the cross-sectional configuration of the opening 69 formed in the developer holding member 68 may be tapered so as to present an increased size toward the photoelectric sensor 59 while reducing toward the light source 58 so that the light from the source 18 cannot irradiate the internal wall of the opening 69. As a further alternative, where the colored component of the developer 23a has a color other than black, a filter of a complementary color to the color of the colored component may be disposed in an optical path between the source 18 and the sensor 19, thus increasing the sensitivity of detection. In addition to determining the level by comparison against a reference value, the detection signal from the photoelectric detector may be used as a level indicating signal which is used in controlling the rate of replenishment of a concentrating toner or may be used control other factors used in an image recording system such as a developing bias value, or control the magnitude of a recording signal. While the inventions described relate to the measurement of the concentration of a liquid developer which is used to develop an electrostatic latent image, the invention is also applicable to any similar colored fluid such as ink used in an ink jet printer of consecutive type or liquid paint used in a painting apparatus.

EXPERIMENT 1

Employing a developer which is prepared by diluting a concentrated toner containing a non-volatile part of 15% in weight ratio into Isopar G (a trade name: Esso Standard Co.): a petroleum group toner dispersion medium, to obtain a volume ratio of 5% status of forming a liquid film in a round-shaped opening is observed.

Thickness of the holding member is 0.5, 1.0, 2.0 and 4.0 mm and diameter of the opening is 0.5, 1.0, 2.0, 3.0 and 4.0 mm$\phi$. The results of the experiment are shown in Table 1.

| Thickness of holding member | Diameter of the opening | | | | | |
|---|---|---|---|---|---|---|
| | 0.5 | 1.0 | 1.5 | 2.0 | 3.0 | 4.0 |
| 0.5 | O | O | O | △ | X | X |
| 1.0 | O | O | O | O | X | X |
| 2.0 | O | O | O | O | O | X |
| 4.0 | O | O | O | O | O | O |

As is shown in Table 1, it is recognized that a good liquid film is formed with the thickness of 0.5 mm when a diameter of the opening is 1.5 mm$\phi$ and less, with the thickness of 1.0 mm when the diameter is 2.0 mm$\phi$ and less, with the thickness of 2.0 mm when the diameter is 3.0 mm$\phi$ and less and with the thickness of 4 mm when the diameter is 4.0 mm$\phi$ and less. In view of the above experimental results, the conditions of forming stable liquid films can be approximated by the following formula.

$$D \leq T + 1/T$$

where a thickness of the holding member is T mm and a diameter of the opening is D mm.

When a liquid film is allowed to stand in the air after formed in the opening, it is observed that the film often bursts with the lapse of time. Also, since a boundary condition of forming a liquid film varies with surface tension of the dispersion liquid, it can be understood that the above approximation formula represents only a criterion for being formable of a liquid film.

When a diameter of the opening is reduced in relation to a thickness of the holding member, a liquid film is certainly formed. However, when the holding member having an opening is put in and out a liquid to be measured, a liquid within the opening is not effectively replaced to cause an error in measurement. In addition, an opening filled with a liquid is allowed to stand in the air and a diameter of the opening is increased in relation to a thickness T, the liquid film bursts in comparatively reduced time and the liquid being measured flows out. At this time, an obstacle to narrow the opening due to sticking of solid components in the liquid being measured is automatically eliminated. In addition, when a diameter of the opening is reduced in relation to a thickness of the holding member, a liquid film is maintained over an increased time and the liquid is enriched by evaporation of volatile components thereof to lower its fluidity. Eventually, all non-volatile components in the liquid which its has been introduced into the opening stick to the wall of the opening to cause variation in diameter such as to affect measured results in a short time. Accordingly, it is desirable that, in measuring concentration of a liquid containing non-volatile components, a diameter D mm of the opening is made larger than a thickness T mm of the holding member. In Table 1, marks O indicate the conditions of preferred configurations in which a liquid film is formed in a stable manner, an excellent replaceability of a liquid is obtained and sticking of non-volatile components can be prevented. As a result, the following approximation formula can be held.

$$T < D < T + 1/T$$

EXPERIMENT 2

Based on the results of Experiment 1, a holding member of 1 mm thick and of a disc of diameter 40 mm is prepared which is provided with only one opening of a diameter 2 mm at a position 15 mm away from the center of the disc. The holding member is rotated with a motor at 10 r.p.m. A photointerrupter EE-SM3(a trade name, Omron Co., Ltd.) of a structure in which a photodiode and a phototransistor are integrally suported is employed as a photoelectric sensor. The photodiode and phototransistor are constructed so as to deliver and receive light through respective openings of 0.8 mm square.

Figure 14:
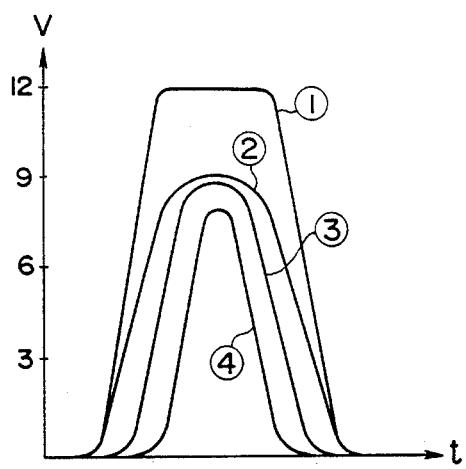
FIG. 14 is a diagram illustrating output waveforms obtained during rotation of the holding member.

A liquid to be measured is a toner of magenta color which has the same concentration as in Experiment 1. A photodiode current of 2.5 mA, an output resistance of the phototransistor of 1.0 KΩ and an applied voltage of 12 V are set so that a high detection sensitivity can be obtained approximately at a toner concentration 5%. FIG. 14 shows output waveforms obtained while the holding member rotates. The ordinate represents a detected voltage developed by the output resistance and the abscissa represents a time. A curve ① shows an output when a liquid to be measured is not supplied within the opening of the holding member under the condition where the center of opening in the holding member is positioned in such a manner that it passes through the opening center of the photointerrupter. A curve ② shows an output waveform when the opening is filled with a liquid to be measured under the same condition as the above. A curve ③ shows an output waveform when a location of mounting the photointerrupter is shifted by 0.25 mm from the center of the opening in the holding member. A curve ④ shows an output waveform when the location is similarly shifted by 0.5 mm.

A photosensitive element of high sensitivity such as a phototransistor has generally a reduced area for receiving light. In addition, when a photoelectric detector whose photometric area is smaller than an opening area for receiving lights and in which a light emitting element is disposed in facing relationship with a photosensitive element through the opening in order to protect both the elements is employed, an output waveform varies depending upon a location of mounting the sensor, as shown in the above experiment. In order to reduce a detection error which is caused by the variation in output, concentration is detected by employing a peak value of output, as described with reference to FIG. 4.

In contrast, although such a method that a detected output is integrated has effects of increasing a total sum of output to thereby improve a signal to noise ratio, the detection is disadvantageously affected by variation in error to a large extent due to a location of mounting a sensor.

It is preferable for the photometric area of photoelectric detector to be small to increase the tolerance of the photoelectric defects to errors in the location at which the detection is mounted. The photometric area cannot be made too small, however, or it will not be able to obtain the required degree of sensitivity. In practice, it is preferred that the photometric area is about no greater than one opening area of the holding member.

When a liquid surface to be measured is in a stationary state, the liquid film can be easily formed as long as the conditions of the above formula are met. However, when the liquid surface is waved or air bubbles are much contained in the liquid, it is difficult to form a liquid film. In practice, however, as shown in FIG. 8, when a liquid to be measured is fed into the concentration measuring apparatus by a pump, since a liquid surface within a developer vessel is waved and air bubbles are much contained in a liquid fed into the vessel, it is impossible to form a liquid film in the opening of the holding member. To eliminate such disadvantages, an apparatus for measuring a concentration needs to provide an auxiliary device for removing air bubbles and eliminating waving of liquid surface.

A variety of such auxiliary devices are known and its structure has no special limitation as long as it serves to feed a liquid into a developer vessel by suppressing and removing air bubbles.

Figure 15:
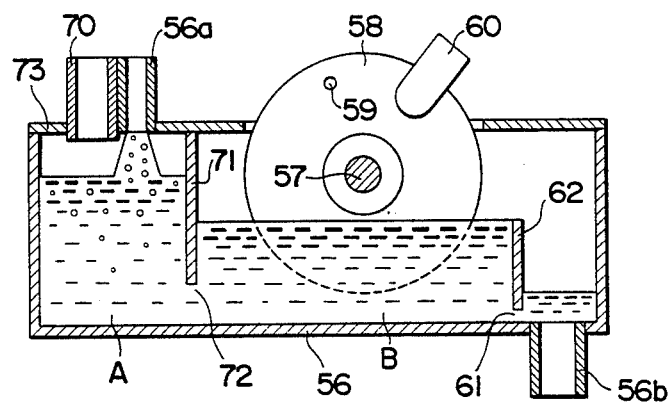
FIG. 15 is a schematic side elevation of an apparatus for measuring concentration according to further embodiment of the invention.

FIG. 15 shows further embodiment an apparatus for measuring concentration of the invention. Like elements are identified by like reference characters. In comparison with the embodiment shown in FIG. 8, the embodiment of FIG. 15 includes a partition plate 71 which divides the vessel 56 into a chamber A for removing air bubbles from the liquid to be measured and a chamber B for supplying the liquid to the opening of the holding member, the partition plate 71 forms a passage 72 which permits communication between the chambers A and B at the lower part of the partition plate 71. To prevent scattering of the liquid, a cover 73 is preferably provided on the top of the chamber A. In this case, there is provided an opening 70 for discharging air contained in air bubbles. Preferably a tube is connected to the opening 70 so as to discharge air into the atmosphere at a position high above the vessel 56. A connector 56a of a pipe for supplying a liquid to be measured also is preferably provided on the top of the chamber A or the cover 73.

A partition 62 is disposed in the vessel 56 to define a small discharge opening 61 along the bottom of the vessel 56. The discharge opening 61 defined by the partition 62 disposed on the bottom of the vessel 56 is not large enough to allow a free and direct passage of the liquid developer. Thus, the liquid developer introduced into the vessel 56 will partly pass through the opening 61, but the level of the developer within the vessel 56 rises rapidly to exceed a level of the partition 62, causing the developer to move beyond the top end of the partition 62, thus stabilizing the liquid level. The stabilized liquid level is chosen to be sufficient to supply the liquid developer into the opening 59 which is positioned so as to be fully immersed when located in a lower position during the rotation of the holding member.

The holding member 58 is driven for rotation by a rotary drive (not shown) to enable the photoelectric detector block 60 to determine the concentration of the developer.

What is claimed is:

1. An apparatus for measuring the concentration of a colored component dispersed in a liquid, said apparatus comprising:
   a vessel for containing a liquid having a colored component dispersed therein;
   a holding member having a thickness T and a substantially circular opening formed therein, said opening being adapted to retain a sample of said liquid, said opening having a diameter D, wherein $D \leq T + 1/T$;
   means for moving said holding member in such a manner that said opening moves between a supply station where it is immersed into said vessel to receive and retain said liquid sample and a measuring station where a measurement of said liquid sample in said opening takes place; and
   photoelectric detector means for measuring the light transmitted through said liquid sample at said measuring station.

2. An apparatus according to claim 1 in which said thickness T of said holding member is less than or equal to said diameter D of said opening.

3. An apparatus according to claim 1 in which said photometric area of said photoelectric detector means is one half of the area of said opening.

4. An apparatus for measuring the concentration of a liquid dispersion, comprising:
- a vessel for containing a liquid dispersion to be measured;
- a holding member having a plurality of substantially circular openings formed therein, each of said openings for receiving and retaining a respective sample of said liquid dispersion, said holding member being peripherally formed with notches at an equal interval to define blades, each of said blades having a respective said opening formed therein, each said blade further being formed with a slit which divides its opening into two equal portions as viewed in the direction of thickness of said holding member;
- means for moving said holding member in such a manner that each of said openings moves between a supply station wherein it is immersed into said vessel to receive and retain said liquid dispersion and a measuring station wherein a measurement of said liquid dispersion in said opening takes place; and
- photoelectric detector means for sequentially determining the light transmission of said sample of liquid dispersion which is retained in each respective opening at said measuring station.

5. An apparatus for measuring the concentration of a liquid dispersion, comprising:
- a vessel for containing a liquid dispersion to be measured,
- said vessel including an inlet disposed on said vessel to allow the entrance of said liquid dispersion into said vessel, an outlet disposed on said vessel to allow the discharge of said liquid dispersion and a depth stabilizing means for maintaining said liquid dispersion in said vessel at a depth sufficient to allow said holding member to be at least partially immersed in said liquid dispersion during the measuring process and for allowing the discharge of said liquid dispersion when the measuring process is completed;
- a holding member having a plurality of openings formed therein, each of said openings for receiving and retaining said liquid dispersion, said holding member being peripherally formed with notches at equal intervals to define blades, each of said blades having a respective said opening formed therein, each said blade further being formed with a slit which divides its opening into two equal portions as viewed in the direction of thickness of said holding member;
- means for moving said holding member in such a manner that each of said openings moves between a supply station wherein it is immersed into said vessel to receive and retain said liquid dispersion and a measuring station wherein a measurement of said liquid dispersion in said opening takes place; and
- photoelectric detector means for sequentially determining the light transmission of said liquid dispersion which is retained in each respective opening as each respective opening is located at said measuring station.

* * * * *